(12) United States Patent
Krogh et al.

(10) Patent No.: US 10,546,101 B2
(45) Date of Patent: *Jan. 28, 2020

(54) THERAPY MANAGEMENT DEVELOPMENT PLATFORM

(71) Applicants: BAXTER INTERNATIONAL INC., Deerfield, IL (US); BAXTER HEALTHCARE SA, Glattpark (Opfikon) (CH)

(72) Inventors: Ross G. Krogh, Long Grove, IL (US); James P. Martucci, Libertyville, IL (US)

(73) Assignees: BAXTER INTERNATIONAL INC., Deerfield, IL (US); BAXTER HEALTHCARE SA, Glattpark (Opfikon) (CH)

( * ) Notice: Subject to any disclaimer, the term of this patent is extended or adjusted under 35 U.S.C. 154(b) by 949 days.

This patent is subject to a terminal disclaimer.

(21) Appl. No.: 14/808,206

(22) Filed: Jul. 24, 2015

(65) Prior Publication Data

US 2015/0332019 A1 Nov. 19, 2015

Related U.S. Application Data

(60) Continuation of application No. 13/682,573, filed on Nov. 20, 2012, now Pat. No. 9,089,643, which is a
(Continued)

(51) Int. Cl.
*A61M 5/172* (2006.01)
*G06F 19/00* (2018.01)
(Continued)

(52) U.S. Cl.
CPC ......... *G06F 19/3468* (2013.01); *A61M 5/172* (2013.01); *G06F 19/3418* (2013.01);
(Continued)

(58) Field of Classification Search
CPC ....... A61M 5/172; G06F 19/363; G06Q 50/22
(Continued)

(56) References Cited

U.S. PATENT DOCUMENTS 4,756,706 A 7/1988 Kerns et al.
4,946,439 A 8/1990 Eggers
(Continued)

FOREIGN PATENT DOCUMENTS

CN 1748219 A 3/2006
CN 1759398 A 4/2006
(Continued)

OTHER PUBLICATIONS

Examination Report No. 1, Australian Patent Application No. 2015261667, dated Jan. 4, 2017.
(Continued)

*Primary Examiner* — Lisa M Caputo
*Assistant Examiner* — Octavia Hollington
(74) *Attorney, Agent, or Firm* — Marshall, Gerstein & Borun LLP

(57) ABSTRACT

A therapy management development platform includes a pump controller coupled to an interface module. The interface module includes an interface module controller and a module-sensor input/output interface including at least one standardized input port, output port and power connection. The interface module is also customizably programmed to receive data from a sensor and to provide instructions to the pump controller to vary the operation of a pump coupled thereto according to one of a plurality of levels of functionality. Upon receipt of an indication of approval from a remote computer to change the level of access to the functionality of the platform, the interface module may be customizably programmed to receive different data from the sensor, to provide different instructions to the pump con-
(Continued)

troller, or both, the approval corresponding to a stage in testing of a medical device.

13 Claims, 11 Drawing Sheets

Related U.S. Application Data division of application No. 12/754,892, filed on Apr. 6, 2010, now Pat. No. 8,315,885.

(60) Provisional application No. 61/169,135, filed on Apr. 14, 2009.

(51) Int. Cl.
*G06Q 50/22* (2018.01)
*G16H 10/20* (2018.01)
*G16H 40/63* (2018.01)

(52) U.S. Cl.
CPC ............ *G06Q 50/22* (2013.01); *G16H 10/20* (2018.01); *G16H 40/63* (2018.01)

(58) Field of Classification Search
USPC .................. 604/65–67, 151–155, 500–522, 604/890.1–892.1; 705/2
See application file for complete search history.

(56) References Cited

U.S. PATENT DOCUMENTS

| | | | |
|---|---|---|---|
| 5,041,086 A | 8/1991 | Koenig et al. | |
| 5,100,380 A | 3/1992 | Epstein et al. | |
| 5,368,562 A | 11/1994 | Blomquist et al. | |
| 5,376,070 A | 12/1994 | Purvis et al. | |
| 5,713,856 A | 2/1998 | Eggers et al. | |
| 5,719,761 A | 2/1998 | Gatti et al. | |
| 5,836,910 A | 11/1998 | Duffy et al. | |
| 5,941,846 A | 8/1999 | Duffy et al. | |
| RE36,871 E | 9/2000 | Epstein et al. | |
| 6,652,447 B2 | 11/2003 | Benkowski et al. | |
| 6,807,965 B1 | 10/2004 | Hickle | |
| 6,985,870 B2 | 1/2006 | Martucci et al. | |
| 7,025,743 B2 | 4/2006 | Mann et al. | |
| 7,044,930 B2 | 5/2006 | Stromberg | |
| 7,074,205 B1 | 7/2006 | Duffy et al. | |
| 7,367,339 B2 | 5/2008 | Hickle | |
| 7,384,410 B2 | 6/2008 | Eggers et al. | |
| 7,415,384 B2* | 8/2008 | Hartlaub ........... | A61M 5/14276 702/182 |
| 7,574,368 B2 | 8/2009 | Pawlikowski et al. | |
| 7,630,773 B2* | 12/2009 | Seeberger .......... | A61N 1/37252 607/59 |
| 7,835,927 B2 | 11/2010 | Schlotterbeck et al. | |
| 7,895,053 B2* | 2/2011 | Holland ................ | G06F 19/326 600/300 |
| 8,038,593 B2* | 10/2011 | Friedman ............. | A61B 5/0002 600/26 |
| 8,315,885 B2 | 11/2012 | Krogh et al. | |
| 8,518,021 B2 | 8/2013 | Stewart et al. | |
| 2002/0029776 A1 | 3/2002 | Blomquist | |
| 2002/0107476 A1 | 8/2002 | Mann et al. | |
| 2003/0114836 A1 | 6/2003 | Estes et al. | |
| 2004/0172283 A1 | 9/2004 | Vanderveen et al. | |
| 2005/0021370 A1 | 1/2005 | Riff et al. | |
| 2005/0135306 A1* | 6/2005 | McAllen .................. | H04L 29/06 370/329 |
| 2005/0144043 A1 | 6/2005 | Holland et al. | |
| 2005/0187515 A1 | 8/2005 | Varrichio et al. | |
| 2006/0030904 A1* | 2/2006 | Quiles ................ | A61N 1/37252 607/60 |
| 2006/0047538 A1 | 3/2006 | Condurso et al. | |
| 2006/0074463 A1 | 4/2006 | Seeberger et al. | |
| 2006/0106649 A1 | 5/2006 | Eggers et al. | |
| 2006/0122867 A1 | 6/2006 | Eggers et al. | |
| 2006/0129433 A1 | 6/2006 | Koneru | |
| 2006/0136271 A1 | 6/2006 | Eggers et al. | |
| 2006/0143051 A1 | 6/2006 | Eggers et al. | |
| 2006/0190302 A1 | 8/2006 | Eggers et al. | |
| 2007/0060870 A1 | 3/2007 | Tolle et al. | |
| 2007/0060871 A1 | 3/2007 | Istoc et al. | |
| 2007/0088249 A1 | 4/2007 | Duffy et al. | |
| 2007/0299389 A1 | 12/2007 | Halbert et al. | |
| 2008/0004601 A1* | 1/2008 | Jennewine .......... | G06F 19/3406 604/890.1 |
| 2008/0052132 A1* | 2/2008 | Iliff ..................... | G06F 19/3418 705/3 |
| 2008/0103531 A1 | 5/2008 | Ginggen et al. | |
| 2008/0132844 A1 | 6/2008 | Peterson et al. | |
| 2008/0140451 A1 | 6/2008 | Hedrick et al. | |
| 2008/0200897 A1 | 8/2008 | Hoss et al. | |
| 2009/0005728 A1 | 1/2009 | Weinert et al. | |
| 2009/0093774 A1 | 4/2009 | Wang et al. | |
| 2009/0099866 A1 | 4/2009 | Newman | |
| 2009/0099867 A1 | 4/2009 | Newman | |
| 2009/0150484 A1 | 6/2009 | Roberts | |
| 2009/0156991 A1 | 6/2009 | Roberts | |
| 2009/0157202 A1 | 6/2009 | Roberts et al. | |
| 2009/0157622 A1 | 6/2009 | Roberts et al. | |
| 2009/0157695 A1 | 6/2009 | Roberts | |
| 2009/0158274 A1 | 6/2009 | Roberts | |
| 2009/0177248 A1 | 7/2009 | Roberts | |
| 2009/0177249 A1 | 7/2009 | Roberts et al. | |
| 2009/0177769 A1 | 7/2009 | Roberts | |
| 2009/0328176 A1 | 12/2009 | Martin et al. | |
| 2012/0221253 A1 | 8/2012 | Hedrick et al. | |
| 2013/0079710 A1 | 3/2013 | Krogh et al. | |
| 2014/0058350 A1 | 2/2014 | Stewart et al. | |
| 2015/0218505 A1 | 8/2015 | Hedrick et al. | |

FOREIGN PATENT DOCUMENTS

| | | |
|---|---|---|
| CN | 1906775 A | 5/2007 |
| JP | 2001344349 A | 12/2001 |
| JP | 2004504912 A | 2/2004 |
| JP | 2004157177 A | 6/2004 |
| JP | 2004516562 A | 6/2004 |
| JP | 2008-516303 A | 5/2008 |
| JP | 2008538243 A | 10/2008 |
| JP | 2009504323 A | 2/2009 |
| JP | 2010536111 A | 11/2010 |
| WO | WO-02/11049 A2 | 2/2002 |
| WO | WO-03/097123 A2 | 11/2003 |
| WO | WO-2006/015002 A1 | 2/2006 |
| WO | WO-2008/097316 A1 | 8/2008 |

OTHER PUBLICATIONS

Notice of Preliminary Rejection (English Translation), Korean Patent Application No. 10-2017-7018100, dated Aug. 31, 2017.
Office Action, Canadian Patent Application No. 2,943,752, dated Jul. 10, 2017.
Australian Patent Application No. 2015261667, Patent Examination Report No. 4, dated Nov. 23, 2017.
Australian Patent Application No. 2015261667, Examination Report No. 2, dated Apr. 18, 2017.
Australian Patent Application No. 2015261667, Examination Report No. 3, dated Jul. 19, 2017.
Canadian Patent Application No. 2758641, Office Action, dated Apr. 22, 2016.
Canadian Patent Application No. 2943752, Office Action, dated Mar. 9, 2017.
Canadian Patent Application No. 2943752, Office Action, dated Nov. 18, 2016.
Korean Patent Application No. 10-2011-7026931, Notice of Final Rejection (with English Translation), dated May 31, 2017.
"Expedited Access for Premarket Approval Medical Devices Intended for Unmet Medical Need for Life Threatening or Irreversibly Debilitating Diseases or Conditions", Draft Guidance for Industry and Food and Drug Administration Staff, U.S. Department of Health

(56) References Cited

OTHER PUBLICATIONS and Human Services, Food and Drug Administration, Center for Devices and Radiological Health and Center for Biologics Evaluation and Research (Apr. 23, 2014).
Business Wire, "ALARIS Medical Systems to Offer Its IEEE 1073 Infusion Pump Communication Software Free on World Wide Web" (Oct. 12, 2009) (2 pages).
Business Wire, "Medical Device Communications Industry Group Announces Web Site Listing of IEEE 1073 Advocate Vendors and Users" (Jun. 2, 2000) (2 pages).
Cardinal Health, Inc., Next Generation Alaris® PC Unit Brochure (2006) (2 pages).
Clarke, "Developing a Standard for Personal Health Devices Based on 11073," *eHealth Beyond the Horizon—Get IT There*, pp. 717-722 (2008).
Goldman et al., "Plug-and-Play in the Operating Room of the Future," *Biomedical Instrumentation & Technology*, pp. 194-99 (May/Jun. 2005).
IEEE Industry Standards and Technology Organization, "IEEE Industry Standards and Technology Organization Announces Formation of New Industry Group" (Feb. 12, 1999) (2 pages).
Notice of Final Rejection, Japanese Patent Application No. 2012-506081, dated Oct. 22, 2014 [English translation].
Notice of Reasons for Rejection, Japanese Patent Application No. 2012-506081, dated Nov. 13, 2013 [English translation].
Notification of the First Office Action, Chinese Patent Application No. 201080016847.9, dated Sep. 12, 2013 [English translation].
Office Action (in English and Japanese), Japanese Patent Application No. 2012-506081, dated Nov. 13, 2013.
Patent Examination Report No. 1, Australian patent application No. AU 2010236758 (dated May 27, 2014).
Patent Examination Report No. 2, Australian Patent Application No. 2010236758, dated Mar. 10, 2015.
Patent Examination Report No. 3, Australian Patent Application No. 2010236758, dated May 29, 2015.
Search Report and Written Opinion, Singapore Application No. 201107267-5, dated May 21, 2013.
Vigilance Medical Technologies, Inc., "Electronic Medical Device Connectivity, Viability and Implementation of the IEEE 1073 Standard" (2002) (5 pages).
Luqi et al., Documentation driven development for complex real-time systems, IEEE Trans Software Engineering, 30(12):936-52 (2004).
Valcke et al., Closed-loop drug infusion for control of heart-rate trajectory in pharmacological stress tests, IEE Trans. Biomedical Engineering, 44(3):185-95 (1997).
Examination Report, European Patent Application No. 10717918.6, dated Feb. 26, 2016.
Notice of Reasons for Rejection (English translation), Japanese Patent Application No. 2015-032551, dated Feb. 25, 2016.
KIPO's Notice of Preliminary Rejection (English Translation), Korean Patent Application No. 10-2011-7026931, dated Dec. 19, 2016.
Examination Report, Canadian Patent Application No. 2758641, dated Mar. 22, 2017.
Canadian Patent Application No. 2,758,641, Office Action, dated Feb. 20, 2018.
Korean Application No. 10-2017-7018100, Notice of Final Rejection, dated Mar. 30, 2018.
Korean Patent Application No. 10-2017-7018100, second Notice of Final Rejection, dated May 30, 2018.
Korean Patent Application 10-2018-7024857, Notice of Preliminary Rejection, dated Sep. 14, 2018.
Korean Patent Application No. 10-2018-7024857, Final Rejection, dated Mar. 28, 2019.
Canadian Patent Application No. 2758641, Office Action, dated Nov. 30, 2018.
Indian Patent Application No. 7878/DELNP/2011, Examination Report, dated Apr. 11, 2019.
Canadian Patent Application No. 2758641, Office Action, dated Nov. 13, 2019.

* cited by examiner

THERAPY MANAGEMENT DEVELOPMENT PLATFORM

This patent is a continuation of U.S. application Ser. No. 13/682,573, filed Nov. 20, 2012, which is a continuation of U.S. application Ser. No. 12/754,892, filed Apr. 6, 2010, which claims the benefit of U.S. Application No. 61/169,135, filed Apr. 14, 2009, all of which are hereby incorporated by reference in their entirety in the present application.

BACKGROUND

This patent is directed to the development of therapy management systems and methods, and, in particular, to the development of therapy management systems and methods that involve modification of the structure and/or operation of a medical device or system used in conjunction with the therapy.

Therapy, or treatment, for a medical condition may be characterized in a number of different ways. For example, therapy may be discussed in terms of the agent used to affect a change in the patient's condition, such as a drug or radiation. As another example, therapy may be discussed in terms of the mode or route of administration.

Infusion therapy—the intravenous delivery (i.e., delivery into a vein) of therapy—is well known in the art. In its simplest form, infusion therapy may be carried out using a container or bag connected to a patient via a drip chamber, an administration set and a catheter. In such a system and according to such a method, fluid passes from the bag to the patient under the influence of gravity. In a more complex system, a pump or a cuff may be used to control the flow of the fluid to the patient.

Improvements to pumping systems used with infusion therapy have included the introduction of pump controllers. Certain pump controllers may be used as a central point for programming one or more pumps. The pump controller may also be used as a central point for displaying information concerning the operation of the pumps and related sensors. Further, the pump controller may be used as a central point for communication between the pumps and sensors and remote computerized systems, such as record-keeping systems for patient information and databases of pharmaceutical information.

Despite the inclusion of the pump controller, infusion therapy management has conventionally involved human intervention, in the form of one or more clinicians administering the process. For example, the clinician may examine the historical data from pump or the patient's chart regarding the therapy (flow rate, volume infused, etc.). The clinician may then combine this data with additional data regarding the patient's condition such as may be obtained from an instrument (e.g., blood pressure cuff, heart monitor, etc.), the patient's chart or the patient directly. Finally, the clinician will exercise his or her medical judgment regarding changes to the therapy.

The development of new therapy management techniques thus typically rely upon a clinician's expertise, and must face the challenge of a rigorous regulation scheme as well. Taking drug delivery as an example, developments tend to occur as to a particular drug and a particular route of delivery. Even in those instances where certain changes of therapy have been automated (e.g., where the pump automatically modifies its operation in accordance with a sensor reading), the development has been isolated to a particular drug and/or required continued intensive clinician involvement to manage the system. Certainly, the nature of the focus is influenced by the need to obtain regulatory approval prior to wide-spread release of the therapy, which approval is only obtained after extensive development and testing of such unique systems. One effect of the isolated nature of development is a proliferation of unique single-use or limited-use systems, methods and/or devices, with the attendant problems of supplying and supporting each of these devices.

As set forth in greater detail below, the present disclosure sets forth an improved assembly embodying advantageous alternatives to the conventional devices and methods discussed above.

SUMMARY

According to an aspect of the present disclosure, a therapy management development platform includes a pump controller and an interface module. The pump controller includes a processor and memory. The interface module includes an interface module controller comprising a processor and memory, and a module-sensor input/output interface comprising at least one standardized input port, at least one standardized output port and at least one standardized power connection. The interface module is coupled to the pump controller. The interface module is also customizably programmed to receive data from a sensor coupled to the module-sensor input/output interface and to provide instructions to the pump controller to vary the operation of a pump coupled thereto according to one of a plurality of levels of functionality. Upon receipt of an indication of approval from a remote computer to change the level of access to the functionality of the platform, the interface module may be customizably programmed to receive different data from the sensor, to provide different instructions to the pump controller to vary the operation of the pump, or both, the approval corresponding to a stage in testing of a medical device, the stage comprising one of bench trials, animal trials, human clinical trials and human use.

BRIEF DESCRIPTION OF THE DRAWINGS

It is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION OF VARIOUS EMBODIMENTS

Figure 1:
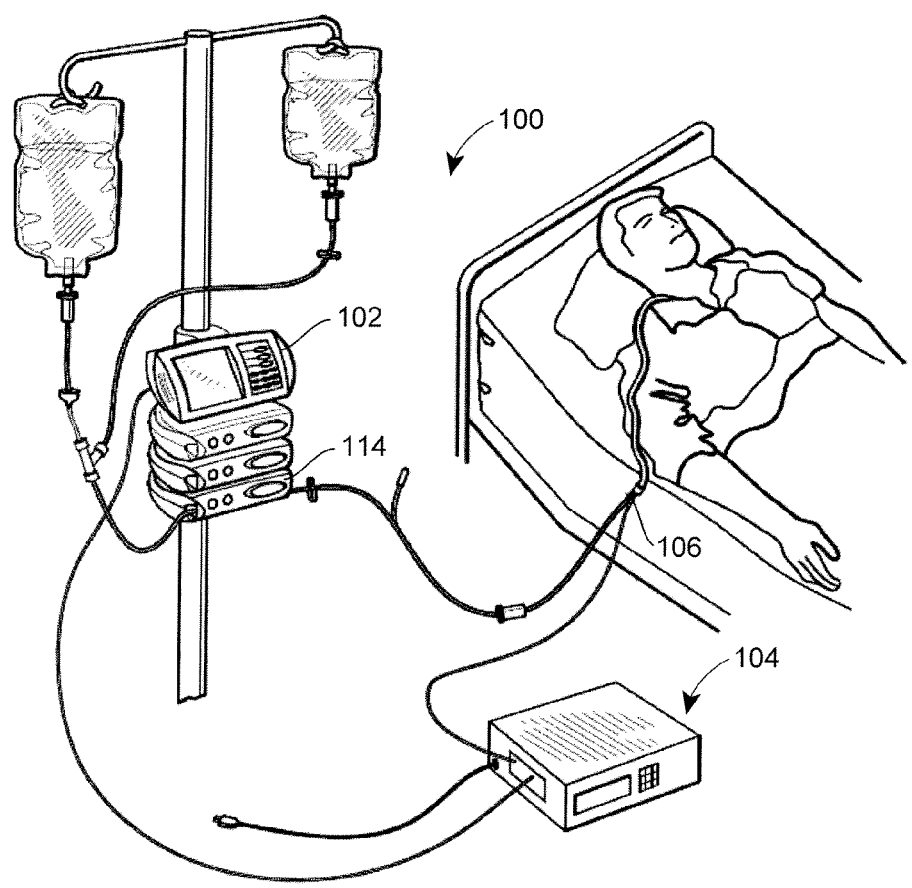
FIG. 1 is a schematic view of a therapy management development platform according to the present disclosure.

Although the following text sets forth a detailed description of different embodiments of the invention, it should be understood that the legal scope of the invention is defined by the words of the claims set forth at the end of this patent. The detailed description is to be construed as exemplary only and does not describe every possible embodiment of the invention since describing every possible embodiment would be impractical, if not impossible. Numerous alternative embodiments could be implemented, using either current technology or technology developed after the filing date of this patent, which would still fall within the scope of the claims defining the invention.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

As noted above, development of new therapy management systems and methods have generally focused on the clinician. This focus may be influenced by the degree to which the experience of the clinician guides the implementation of many therapy management systems and methods. Certainly, this focus has its limitations, in that while the clinician may be experienced in the treatment of a particular medical conduction or the use of a particular delivery system or drug, for example, the clinician may not be experienced in the actual design and operation of the delivery system used. Given the rigorous testing that must be conducted and therefore the level of knowledge of the structure and operation of the system required, the barriers to variation of the delivery system as part of a new therapy are high, especially upon the advent of sophisticated control devices, such as pump controllers.

On the other hand, the advancement of medical science would be benefited from a shift from the skills and experience of the clinician, at least as to variations in equipment, to those of the medical device manufacturer. The medical device manufacturer, while lacking the degree of sophistication of the clinician in their understanding of the patient's response to particular therapies, has a deep and thorough knowledge of the structure and operation of medical devices and systems. As such, variation of the structure and the operation of the device may represent a less impressive barrier to the manufacturer than to the clinician.

While recognizing that the traditional model for clinician/manufacturer development has involved an intensive partnership between the two parties, it is believed that a more standardized approach to the issue of therapy management development may provide for advantages to both parties. In particular, it is believed that the organized and standardized set of tools, both hardware and software, presented herein will provide greater access to the clinician, while at the same time decreasing the need for intimate interaction with the manufacture on a daily basis. Further, safeguards may be included in the system to decrease the likelihood that development will subvert existing regulatory framework.

FIG. 1 illustrates schematically an embodiment of a therapy management development platform. In particular, this platform is useful for designing sensors to be used in conjunction with a pump for use in intravenous (IV) infusion therapy, and in particular for closed-loop IV infusion therapies, such as IV drug control. However, as it will be recognized and as explained herein, the therapy management development platform may be used in conjunction with other therapies provided by other medical devices as well.

Figure 2:
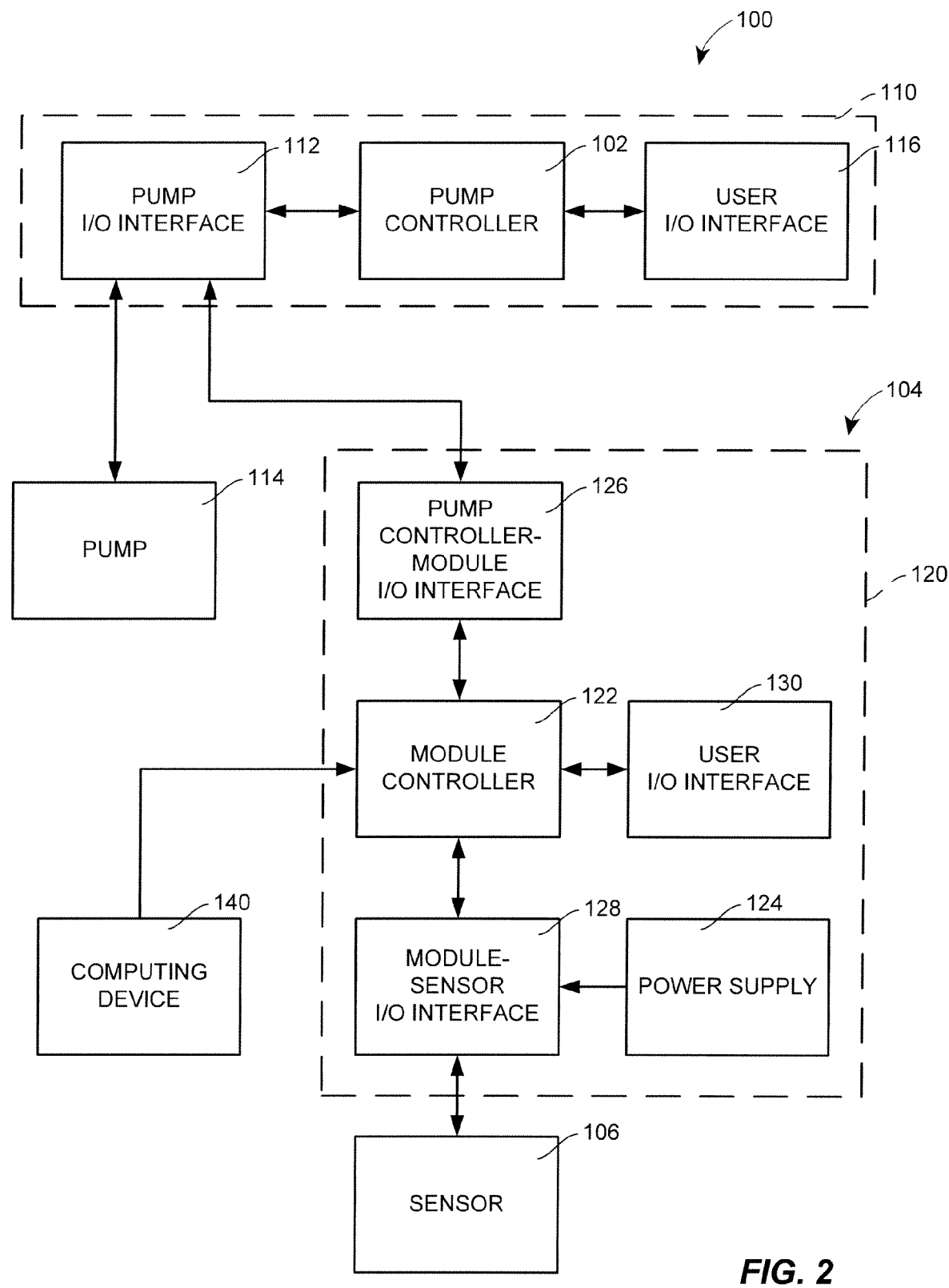
FIG. 2 is a block diagram of the platform of FIG. 1.

As seen in FIGS. 1 and 2, a therapy management development platform, or system, 100 according to the present disclosure is illustrated. The system 100 may include a pump controller 102, an interface module 104, and a sensor 106. The pump controller 102 and the interface module 104 communicate with each other, as do the interface module 104 and the sensor 106. Each element of the system 100 will be explained in greater detail below.

As illustrated in FIGS. 1 and 2, the pump controller 102 may be disposed or mounted in a housing 110. The housing 110 may be configured to be attached to a stand such as may be used to support therapy elements of the like. Alternatively, the housing 110 may be configured to sit on a surface, such as desk top or the like.

The pump controller 102 may include a processor and memory. The memory may be in form of read-only memory (ROM) and random access memory (RAM). The ROM may take many different forms, including erasable programmable ROM (EPROM) and electrically erasable programmable ROM (EEPROM).

The pump controller 102 may be coupled to a pump input/output (I/O) interface 112. The pump I/O interface 112 is configured to permit the pump controller 110 to communicate with one or more pumps 114 associated with the pump controller 102. The communication between the pump or pumps 114 and the controller 102 may be carried out over a hardwired connection or wirelessly, through the use of radio-frequency (RF) or infra-red (IR) transmitters and receivers, for example. A wide variety of communication protocols may be used, such as wired Ethernet, wireless Ethernet (Wi-Fi), ZigBee, and Bluetooth.

The pump controller 100 may also be coupled to a user I/O interface 116. The user I/O interface 116 may include one or more output devices, such as a visual display (such as a liquid crystal display (LCD) or a light emitting diode (LED) display) and/or an audible display (such as a piezoelectric buzzer). Such output devices may be used to provide key interaction events to delineate how therapy control is affecting outcome parameters, e.g., multi-variable graphs with marked events. The user I/O interface 116 may also include one or more input devices, such as push buttons, touch-screen panels, keyboards, and the like; the input devices may also include readers for use with barcode, RFID, magnetic stripe or holographic image technologies. The user I/O interface 116 may be used to access information stored within the pump controller 102 (such as flow history, volume delivered, delivery interruptions, flow rates, and drug sensitivity information) and/or to program the pump controller 102 to control the operation of the one or more pumps 114.

The interface module 104 may also include a number of different subsystems, all of which may be disposed or mounted in a housing 120. As illustrated, the interface module 104 includes a module controller 122, a power supply 124, a pump controller-module I/O interface 126, a module-sensor I/O interface 128, and a user I/O interface 130. The housing 120 may be configured to be connected to or mounted on a stand, similar to the housing 110, or may even be configured to be connected to or mounted on the housing 110.

Like the pump controller 102, the module controller 122 may include a processor and memory. The memory may be in form of read-only memory (ROM) and random access memory (RAM). The ROM may take many different forms, including erasable programmable ROM (EPROM) and electrically erasable programmable ROM (EEPROM).

The pump controller-module I/O interface 126 is coupled to the module controller 122 and permits communication with the pump I/O interface 112, perhaps according to one or more standardized communication protocols, such as are being formulated by the International Standards Organization (ISO) and (IEEE) through the incorporation of the Integrating the Healthcare Enterprise (IHE) processes. As was the case with the pump(s) 114, the communication between the pump controller-module I/O interface 126 and the pump I/O interface 112 may take the form of a hardwired or wireless connection. The pump controller-module I/O interface 126 may be configured to the particular proprietary hardware and software specifications of the pump controller manufacturer.

The module-sensor I/O interface 128 has at least one standardized input port, at least one standardized output port and at least one standardized power connection. The module-sensor I/O interface 128 is also coupled to the module controller 122 and the power supply 124, with the communication between the interface 128 and the controller 122 permitting the controller 122 to communicate with the sensor 106 and the connection between the interface 128 and the power supply 124 to provide power to the sensor 106.

The user I/O interface 130 is coupled to the module controller 122 and is similar to the user I/O interface 116. The user I/O interface 130 may include one or more output devices, such as a visual display (such as a liquid crystal display (LCD) or a light emitting diode (LED) display) and/or an audible display (such as a piezo-electric buzzer). Such output devices may be used to provide key interaction events to delineate how therapy control is affecting outcome parameters, e.g., multi-variable graphs with marked events. The user I/O interface 130 may also include one or more input devices, such as push buttons, touch-screen panels, keyboards, and the like. However, unlike the user I/O interface 116, the user I/O interface 130 may not have dedicated text-based interface or graphical user interface (GUI) associated with the output devices or dedicated icons or pictograms assigned to the input devices. The absence of such dedicated assignments is discussed in greater detail below.

In addition to being coupled to the interfaces 126, 128, 130, the module controller 122 may also be in communication with a computing device 140. The communication with the computing device 140 may be hardwired or wireless. The communication may also be continuous or discrete; that is, the controller 122 may be coupled to the computing device 140 through the use of a cable or transmitter/receiver connection, or one or more memory devices (e.g., memory sticks) may be used to transport programs prepared using the computing device 140 to the controller 122. While not shown, a further interface may be disposed between the controller 122 and the computing device 140 to permit communication between the devices.

In particular, the computing device 140 may include one or more applications (which may be collectively referred to as a development toolkit) that facilitate programming of the controller 122. These applications may permit a program to be written by a user through the manipulation of a GUI in combination with a library of standardized input commands, output commands, and procedure commands. The user would thus be able to select from the input commands, output commands and procedure commands to compose a program, which the application would automatically convert into a language understood by the controller 122. This may be achieved with greater efficiency using the development toolkit than without.

For example, a user may select input and output commands to establish data channels to receive signals from the sensor 106, signals from the pump controller 102 and signals from the user I/O interface 130. The user may also use standardized commands to scale the inputs according to ranges of the signal outputs from the sensor 106 and pump controller 102. Further, the user may select filtering algorithms from the procedure commands to, for example, filter the data received from the sensor 106 and the pump controller 102. The user may also select control algorithms that implement one or more standardized control models. Furthermore, these control algorithms could be represented in the GUI through the use of intuitive representations and symbology, rather than complicated expressions of these complex algorithms. Unit correction could be handled automatically based on the input, output, and procedure commands selected.

As a more particular example, the user may have a new glucose sensor to be used in a closed-loop drug delivery control system. The user may use the development toolkit to assign certain channels of the pump controller I/O interface 126 to retrieve pump data, to assign certain channels of the sensor-module I/O interface 128 to retrieve sensor data, and to configure the user I/O interface 130 to display information on or controls for the parameters of interest (blood glucose, glycosolated hemoglobin, IV insulin infusion flow rate, and oral and IV nutritional inputs). The user may use the scaling tools to scale the glucose readings according to the minimum and maximum voltage outputs for the sensor 106, and the pump flow rate and inputs according to the nutritional scale selected. The user may also select filtering algorithms to eliminate noise from the sensor data (e.g., a 3-pole, low pass filter), and to eliminate user data entry errors from the input data. The user may also select an available control model from a library, with the only input being selection of the loop gains and feedback sources for each component of the model. The application would then automatically perform integrity checks (such as for mathematical unit consistency and conversions) and generate a program, complete with the necessary system equations, that could be uploaded to the controller 122.

Of course, while it may be suggested from the discussion above that the computing device 140 may be disposed in the same general area as the controller 122 to permit uploading via a local hardwired or wireless connection, or uploading of the program to a controller 122 from a portable memory device moved between devices occupying space in the same room, this need not be the case according to all implementations of the system 100. For example, a computing device 140 may be disposed in a location remote to the system 100, and the program (once generated) may be transmitted electronically over a computer network (such as a wide area network, an intranet or the Internet). As a consequence, the action of uploading may involve the movement of the program across great geographic distances between the computing device 140 and the system 100.

Figure 3:
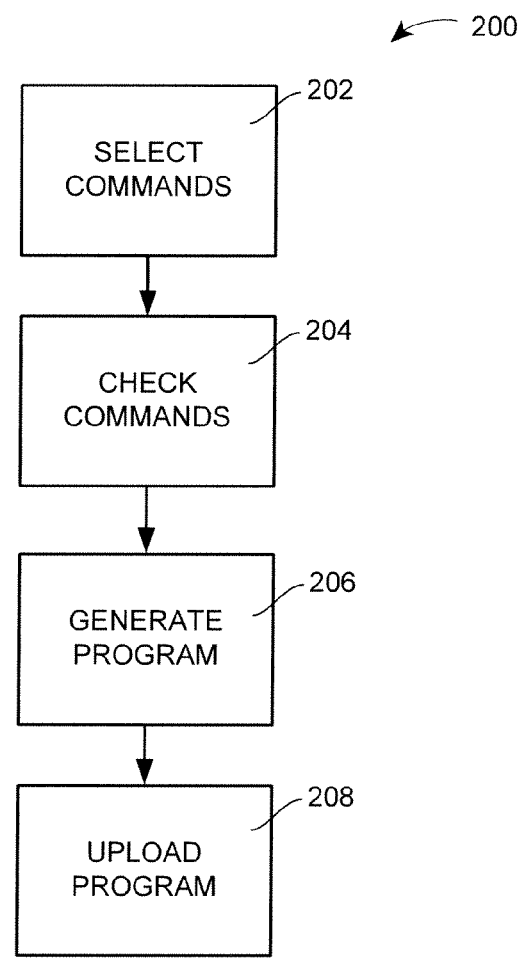
FIG. 3 is a flowchart of a method of preparing a program for the sensor module of the system according to FIG. 1.

Thus, FIG. 3 shows a simplified method 200 according to the present disclosure, wherein user uses a computing device 140 running the development toolkit application to select commands from a standardized library of commands for programming the module controller 122 at block 202. The computing device 140 then performs certain checks on the commands selected at block 204, and converts the commands to generate a program in a language understood by the module controller 122 at block 206. The program may then be uploaded to the module controller 122 at block 208.

Figure 4:
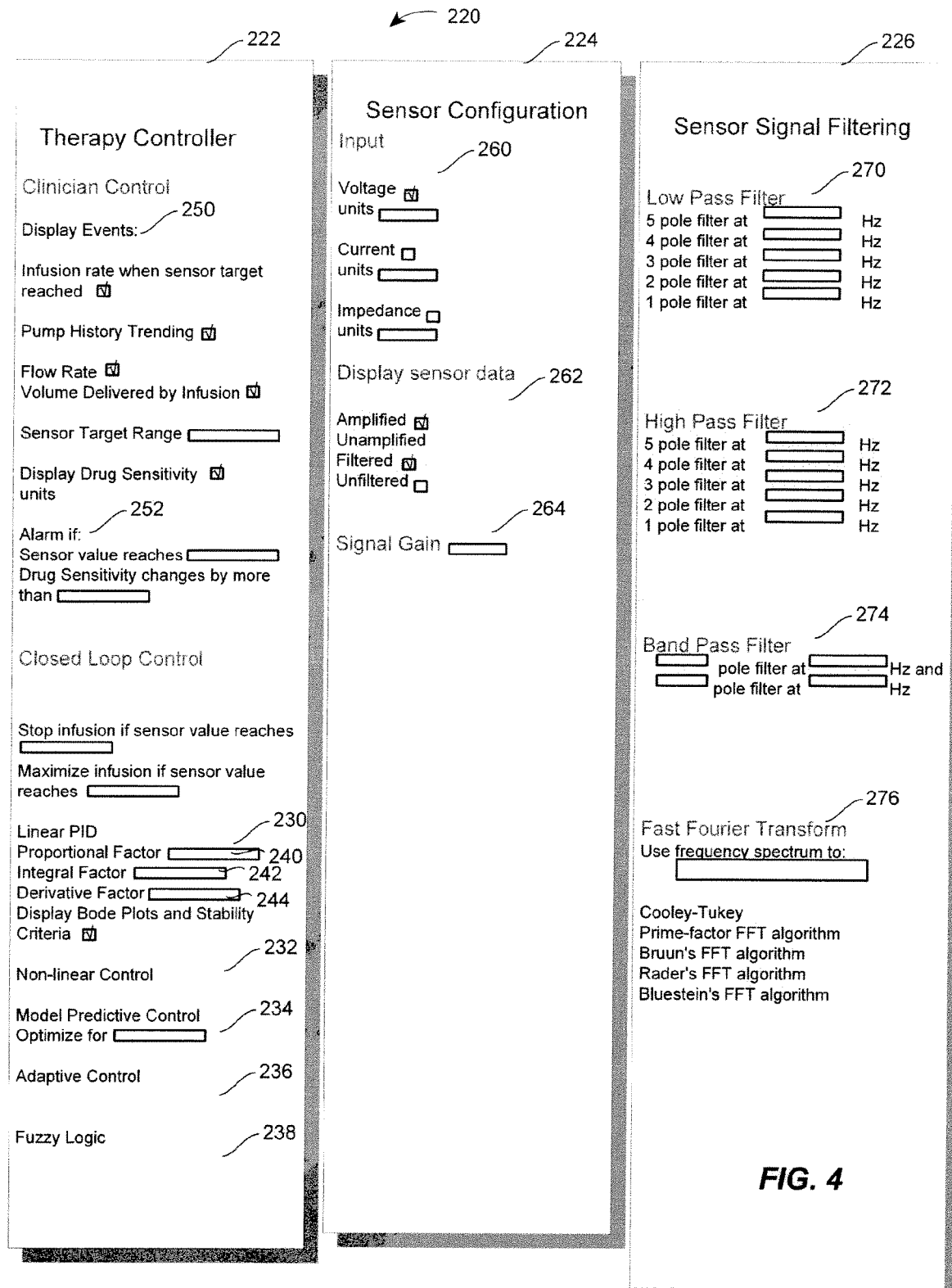
FIG. 4 is an illustration of the development tool used in programming of the sensor module.

FIG. 4 is a representation of the graphical user interface 220 displayed to the user by the development tool kit operating on the computing device 140. The graphic user interface 220 is merely an exemplary embodiment; it will be recognized that other interfaces are also possible.

According to the illustrated embodiment, the interface 220 includes a plurality of user options. For convenience and ease of implementation, the user options are organized into three groups or categories: therapy control options 222, sensor configuration options 224 and filter configuration options 226. Within each group 222, 224, 226, there may be a plurality of user options, as illustrated. However, it is also possible to have a group defined by a single user option, and it is possible to have all of the user options organized into a single group.

Each of the user options within each group 222, 224, 226 may be associated with one or more objects, routines, programs, etc., the configuration of these objects, routines, programs, etc. being influenced by the user options selected or modified within the one or more groups 222, 224, 226. For example, within the therapy control option group 222, there are options for linear PID control 230, non-linear control 232, model predictive control 234, adaptive control 236, and fuzzy logic control 238. Selecting any one of the options 230, 232, 234, 236, 238 may use a particular object, routine, program, etc. to the exclusion of objects, routines, programs etc. for the other options. As such, a radio button may be used so that the user may select only one of the options 230, 232, 234, 236, 238.

Moreover, the user options may be organized using a tree structure, such that a selection of a first user option may lead to further options being available to the user, while other options are excluded. For example, if the linear PID control option 230 is selected, there are further options 240, 242, 244 for setting a proportional, integral or derivative factor. While the further options 240, 242, 244 are illustrated as being displayed at the same time as the options 230, 232, 234, 236, 238, the options 240, 242, 244 may be displayed only if the linear PID control option 230 is selected. As another option, a pull-down list or other GUI control may be used to display the options possible within the linear PID control option 230 (or any of the other options for that matter).

It will also be recognized that the user options 230, 232, 234, 236, and 238 are all options for closed loop control of the system of the therapy management including the pump 114. Within the control group 220, there are also options for clinician control as well. This illustrates that within each group 220, the user options may be further organized into subgroups as well. For the clinician control, user options may focus on the display of information for user by the clinician, as well as the setting of boundary conditions to prevent inadvertent user error.

For example, the user options under clinician control include display options 250 and alarm options 252. The display options 250 may include display of flow rates and volumes, as well as historic information on pump operation. The alarm options 252 may include options for when to set off audible and/or visual alarms, either in terms of changes in sensor output or some other condition, such as drug sensitivity. The options 250, 252 also highlight the fact that the user options do not necessarily require an input in the form of a numeric value or a pull-down list, but may simply be in the form of a check box.

In regard to the sensor group 222, user options for sensor input 260, display 262, and gain 264 may be selected. As was the case with the user options within the control group 220, the user options for input 260, display 262, and gain 264 are associated with objects, routines, programs, etc. that are influenced by the selections made. Further, some of the options are mutually exclusive—the amplified/unamplified option and filter/unfiltered option under the display subgroup 262 are examples. Other options require the user to provide a numerical value, such as the gain subgroup 264.

Finally, in regard to the filter group 224, user options are available to select objects, routines, programs, etc. that will perform filtering of the data from the sensor 106 before it is used in the control algorithm. Possible options may be organized into low pass, high pass, and band pass subgroups 270, 272, 274. An subgroup 276 for user options regarding use of Fast Fourier Transforms (FFT) may also be provided. As illustrated, each one of the subgroups may have a plurality of options associated therewith.

Having thus discussed the system 100, the method 200 of use of the development tool kit, and an exemplary embodiment of a GUI 250 associated with the development tool kit, it will be recognized that the system 100 may include one or more additional aspects, which aspects may provide additional advantages to the system 100.

For example, the system 100 may be used with a standardized sensor platform for the sensor 106 permitting the sensor 106 to be connected to the sensor-module I/O interface 130. The platform, which may be in the form of a catheter, may include standardized leads for data collection and power distribution. As a consequence, the user may focus on development of the sensor or transducer, rather than on the mechanism to position, power and/or communicate with the sensor relative to a patient.

Additionally, the system 100 may feature a lockout process that prevents a sensor or a program from being used with the pump controller 102 without use of the interface module. The lockout process may include a hardware component and/or a software component. More typically, the lockout process will be in the form of a software component, such as a password or encryption. The lockout may enable or prevent use of the system in specific locations prior to regulatory approval, as explained in greater detail below.

In this regard, the lockout process may be configured so as to permit different levels of access. For instance, at a first level, the system 100 may deny any operational privileges to the system 100. At a second level, the system 100 may permit the system 100 to be used for investigational use only. Finally, at a third level, the system 100 may permit use of the system 100 once regulatory approval has been obtained.

It will also be recognized that while FIGS. 1-4 represent an embodiment of a therapy management development platform according to the present disclosure, other alternative embodiments are possible. Exemplary additional embodiments are illustrated in FIGS. 5-7.

Figure 5:
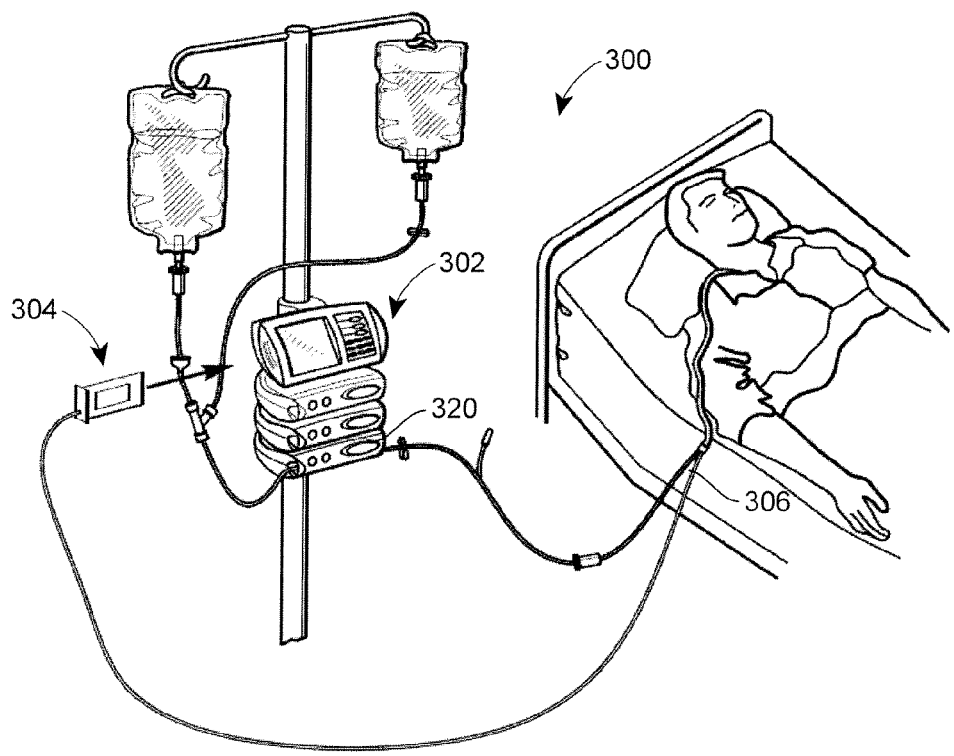
FIG. 5 is a schematic view of an alternative therapy management development platform according to the present disclosure.
Figure 6:
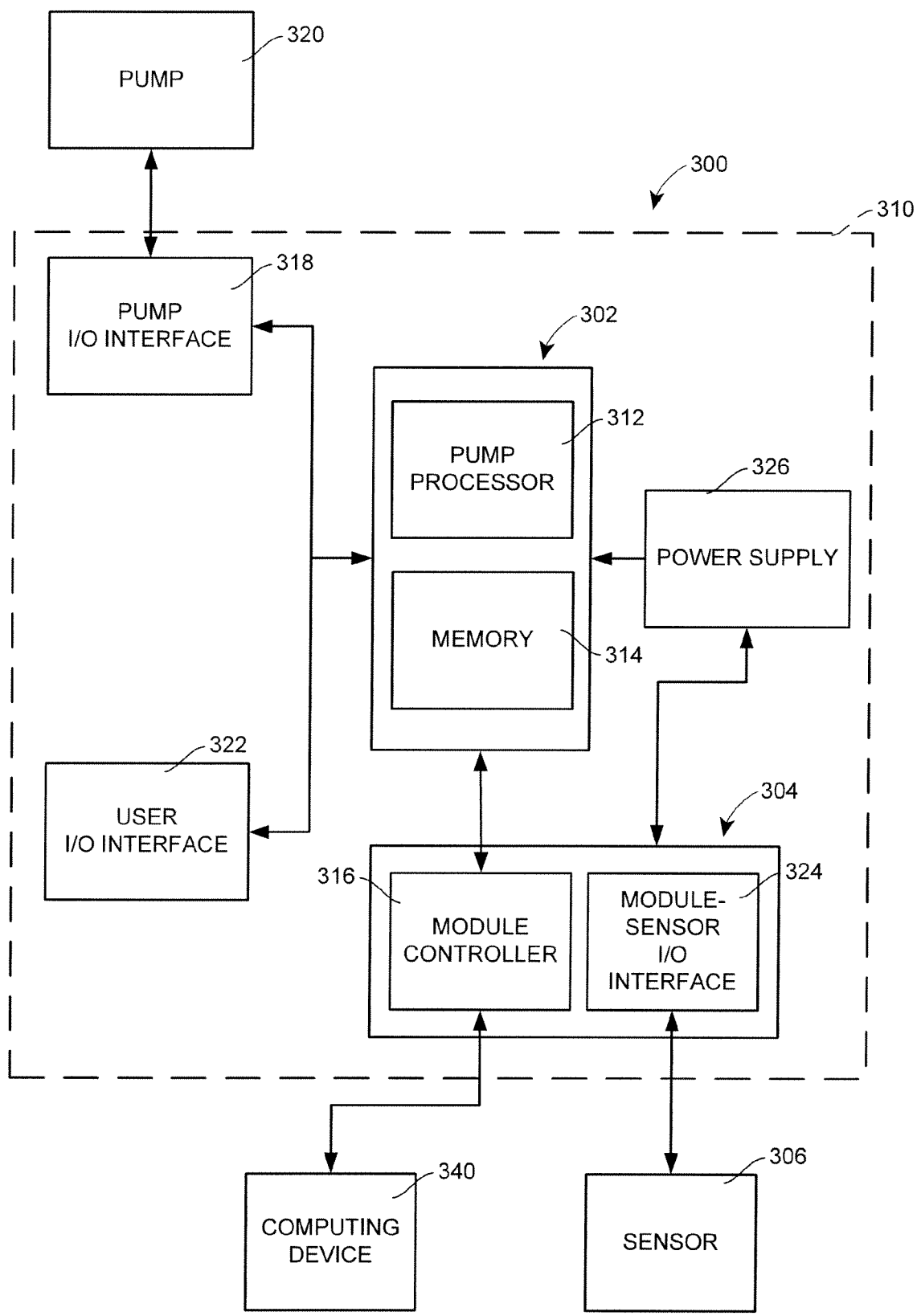
FIG. 6 is a block diagram of the platform of FIG. 5.
Figure 7:
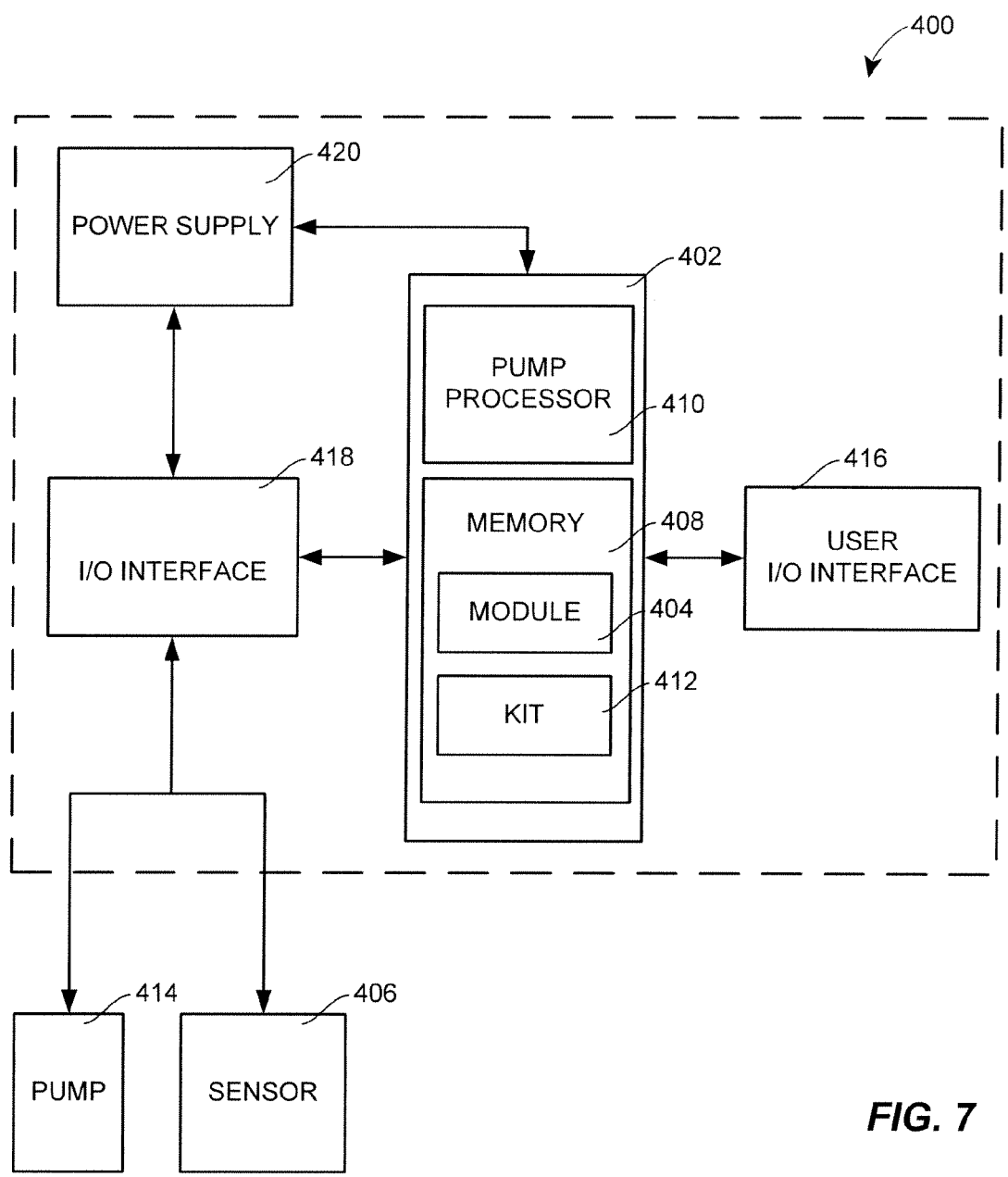
FIG. 7 is a block diagram of a further alternative therapy management development platform according to the present disclosure.

FIGS. 5 and 6 illustrate an exemplary alternative embodiment wherein the module does not reside outside the housing of the pump controller. As such, the module, which may still retain its own processing and memory, may utilize other aspects of the pump controller, such as the integral power supply of the pump controller so reduce equipment requirements and costs. The separation of the processing and memory of the module permits the embodiment of FIGS. 5 and 6 to facilitate logical decomposition of the system, as well as safety and effectiveness by establishing boundaries between the subsystems of the system.

Referring then to FIGS. 5 and 6, it will be recognized that a therapy management development system 300 includes a pump controller 302, an interface module 304, and a sensor 306. The pump controller 302 and the interface module 304 communicate with each other, as do the interface module 304 and the sensor 306.

As mentioned above, the pump controller 302 and the interface module 304 may be disposed or mounted in a single housing 310. The housing 310 may be configured to be attached to a stand such as may be used to support therapy elements of the like. Alternatively, the housing 310 may be configured to sit on a surface, such as desk top or the like.

Both the pump controller 302 and the module 304 may include a processor and memory. In the instance of the pump controller 302, the processor 312 and the memory 314 are represented separately, while the processing and memory capabilities of the module 304 are represented in the form of a module controller 316. The memory may be in form of read-only memory (ROM) and random access memory (RAM). The ROM may take many different forms, including erasable programmable ROM (EPROM) and electrically erasable programmable ROM (EEPROM).

The pump controller 302 may be coupled to a pump input/output (I/O) interface 318. The pump I/O interface 318 is configured to permit the pump controller 302 to communicate with one or more pumps 320 associated with the pump controller 302. The communication between the pump or pumps 320 and the controller 302 may be carried out over a hardwired connection or wirelessly (through the use of radio-frequency (RF) or infra-red (IR) transmitters and receivers, for example).

The pump controller 302 may also be coupled to a user I/O interface 322. The user I/O interface 322 may include one or more output devices, such as a visual display (such as a liquid crystal display (LCD) or a light emitting diode (LED) display) and/or an audible display (such as a piezoelectric buzzer). Such output devices may be used to provide key interaction evens to delineate how therapy control is affecting outcome parameters, e.g., multi-variable graphs with marked events. The user I/O interface 322 may also include one or more input devices, such as push buttons, touch-screen panels, keyboards, and the like. The user I/O interface 322 may be used to access information stored within the pump controller 302 (such as flow history, volume delivered, delivery interruptions, flow rates, and drug sensitivity information) and/or to program the pump controller 302 to control the operation of the one or more pumps 320.

The interface module 304 may also include a number of different subsystems, which may be disposed or mounted with the module controller 316 on a card that is received in a card slot on the pump controller 302. As illustrated, the interface module 304 includes a module-sensor I/O interface 324. As is also illustrated, the interface module 304 may be disposed substantially within the same housing 310 as the pump controller 302.

The module-sensor I/O interface 324 may have at least one standardized input port, at least one standardized output port and at least one standardized power connection. The module-sensor I/O interface 324 is also coupled to the module controller 316 and a power supply 326, which power supply 326 is also used by the pump controller 302. In this fashion, the interface module 304 is capable of utilizing elements typically associated with the pump controller 302 to reduce the overall equipment requirements and costs of the module 304.

In addition, the module controller 316 may interface with the pump controller 302 so as to communicate with the user I/O interface 322 associated with the pump controller 302. As such, the embodiment of FIGS. 5 and 6 is able to leverage the existing equipment of the pump controller 302, and reduce the costs of the module 304. Of course, the minimum requirements of the pump controller 302 are different than those of the controller 102 in that the module 304 will need to access the user interface 322 through the controller 302 as illustrated. It will be recognized that according to a further alternative embodiment, the user I/O interface 322 may be configured such that the module controller 316 may communicate with the interface 322 in parallel to the pump controller 302, rather than in series through the pump controller 302.

As for the programming of the module controller 316, the module controller 316 may also be in communication with a computing device 340. The communication with the computing device 340 may be hardwired or wireless. The communication may also be continuous or discrete; that is, the controller 316 may be coupled to the computing device 340 through the use of a cable or transmitter/receiver connection, or one or more memory devices (e.g., memory sticks) may be used to transport programs prepared using the computing device 340 to the controller 316. In this fashion, the module controller 316 may be programmed without having to rely on the user I/O interface 322 having the capabilities to manipulate the development tool kit operating on the computing device 340.

A still further embodiment of the therapy management development system 400 is illustrated in FIG. 7. According to this embodiment, a pump controller 402 is configured to operate similar to the pump controllers 102, 302, but is also configured with sufficient I/O interfaces, processing capability and memory capacity so as to reduce the module 404 to software operating in the pump controller 402 and to permit the module 404 to be programmed without resort to a separate computing device. As such, the pump controller 402 is significantly more dedicated to use with the module 404 than the pump controllers 102, 302, which may be decoupled from the modules 104, 304 and used in their more traditional role.

As illustrated, the system 400 includes the pump controller 402, the module 404 and a sensor 406. As noted above, the module 404 resides in memory 408 associated with the pump controller 402, and it operable on the processor 410 associated with the memory 408. The memory 408 may also include a development tool kit 412 for use with the module 404 to program the module to carry out the data acquisition with the sensor 406 and potentially a modified therapy management routine with a pump 414.

To permit the pump controller 402 to be used to program the module 404 through the use of the tool kit 412, it may also be required that the user I/O interface 416 be configured differently than the user I/O interfaces of the embodiments of FIGS. 1 and 5. Similarly, if the I/O interface 418 is to be used to supply power to the sensor 406 from the associated power supply 420, then the interface 418 may have capabilities different from and in addition to the capabilities of the interfaces of the embodiments of FIGS. 1 and 5.

Figure 8:
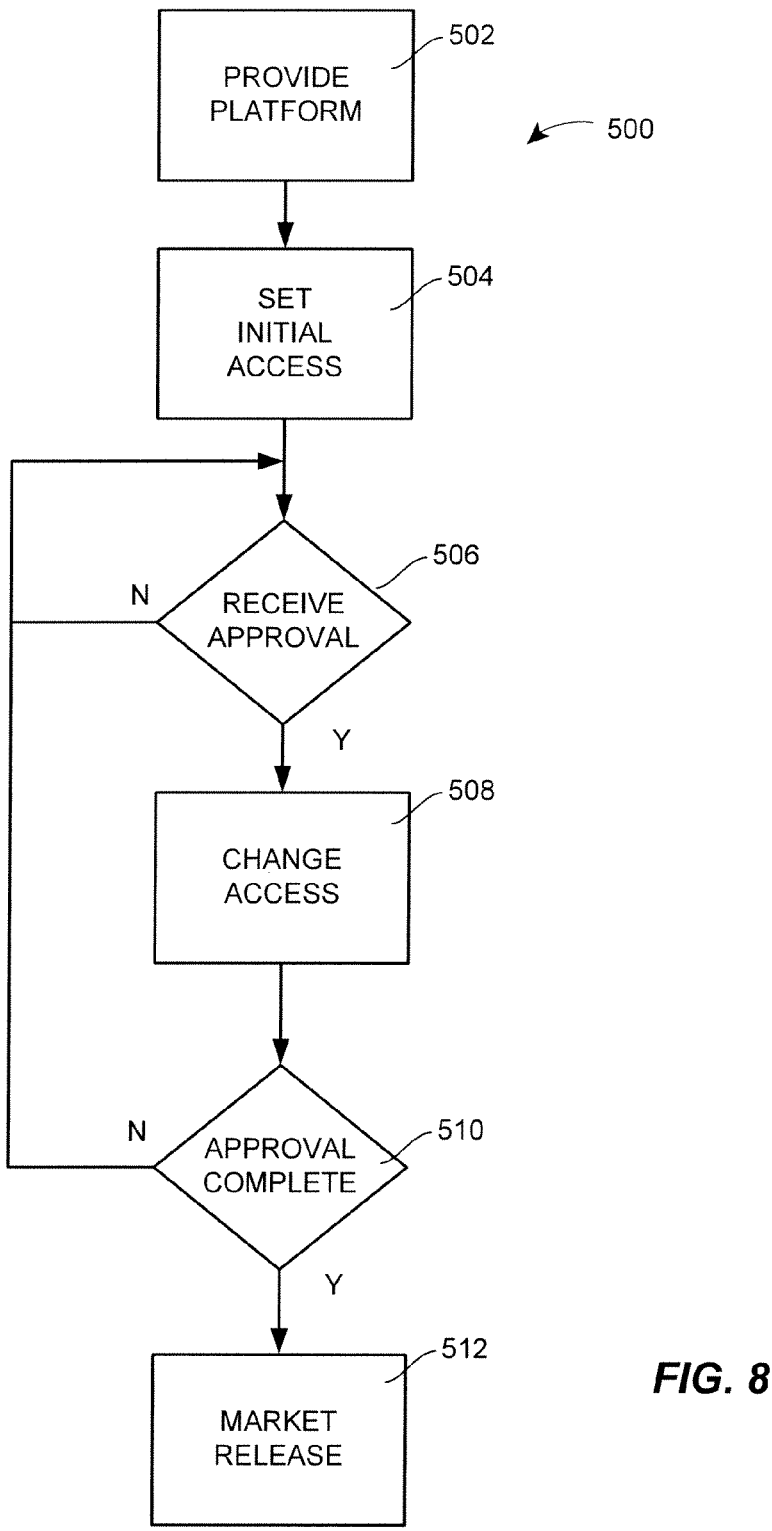
FIG. 8 is a flowchart of the method using the systems according to the preceding embodiments to provide a controlled testing format for device approval.

Having thus discussed several different embodiments of a therapy management development platform and their use by the developer/clinician, FIG. 8 illustrates the use of these platforms as part of a method 500 of controlled, standardized testing to obtain approval for the medical devices or methods developed using the platform. As will be recognized, many medical devices or systems require approval prior to marketing. In certain jurisdictions, this approval is provided by governmental bodies, while elsewhere it may be provided by independent commercial organizations that are accountable to governmental bodies. The approval process may require a series of stages of testing (bench, animal, human clinical, and fully approved use on humans ("human use")), and the stages may even have clearly defined phases (pilot, pivotal). The method 500 uses the platforms described above to assist in controlling therapy management development to ensure that proper testing has been performed.

At block 502, the platform is provided to a therapy management developer by the platform manufacturer or a party associated with the manufacturer. The platform may be, for example, designed in accordance with one of the embodiments illustrated above in FIGS. 1-7. As will be recognized, these platforms have the ability to be used in conjunction with or as a pump controller to vary the operation of an associated pump in an infusion therapy. As will be detailed below, other platforms may also be provided that are useful, for example, with renal therapy or inhalation therapy.

As will be recognized, these platforms may have a plurality of levels of functionality relative to the medical device (e.g., pump controller and pump) that permits the platforms to be used in bench testing, in animal testing or trials, and in clinical (or human) testing or trials. However, it will also be recognized that typically bench testing and animal trials precede clinical trials, and that even within the scope of clinical trials, different phases may be passed through sequentially in the process of obtaining approval for the device or system. Moreover, it is believed that control of the use of the platform to ensure that the testing or trials proceed in the required fashion to obtain approval is important.

Consequently, at block 504, the platform will be provided to the user with the platform set to an initial level of access to the functionality relative to the medical device. The initial level of access may, in many cases, be suitable for conducting bench trials using the user-defined sensor or control algorithm. However, it will also be appreciated that while certain advantages may be obtained by using the platform for all of the required testing (bench, animal, clinical), other advantages may also be obtained by utilizing the platform once initial bench testing, for example, is completed. Consequently, the initial level of access may not correspond with use of the platform for bench testing utilizing the platform in all cases.

The access to a certain level of functionality of the device may be achieved through the use of the lockouts described above. That is, a particular password or encryption key may provide the developer with access to the functionality of the device useful for bench trials, but not for animal or clinical trials. A different password or encryption key may provide access to functionality for bench, animal and clinical trials, and so on.

The developer is then able to modify the operation of the medical device using the platform, as described above. For example, the developer may use a prototype sensor with the medical device through the use of the platform. Alternatively, the developer may make changes to the operation of the control algorithm used by the medical device to control therapy management, in particularly by using the developer toolkit. As a further alternative, the developer may use a prototype sensor and change the operation of the control algorithm. In any event, the modification of the operation of the medical device using the platform, according to the present disclosure, does not mean changing the operation of the medical device so as to simply vary an amount or rate of therapy provided to the patient (i.e., the modifications are non-surgical and non-therapeutic in and of themselves). According to the present disclosure, the medical device is capable of providing a first functionality (capability of using certain sensors or control algorithms) prior to modification using the platform, and a second functionality after modification using the platform (capability of using additional or different sensors and/or control algorithms). Whilst the medical device itself may, of course, be used to provide beneficial therapy to a patient, the claimed methods are performed without providing any therapeutic benefit to a human or animal; ie the claimed methods are non-therapeutic. Also, the claimed methods do not involve any surgical step performed on the body of a human or animal; ie the claimed methods are non-surgical.

The method 500 then continues to block 506, wherein the party controlling access to the functionality of the platform makes a determination if it has received indication that the developer has received approval to proceed to a new level of access to the functionality of the platform, permitting further testing to occur. This indication may be provided by the developer, or by a party working in association with the developer (e.g., an institutional review board), or by the governmental/independent organizations mentioned above. For that matter, the approval may be determined by the party that controls access to the platform, and thus need not be a party separate and apart from the party that controls access to the platform.

If no approval to advance to the next level of access has been received, the method 500 remains at block 506. If approval is received, then the method 500 proceeds to block 508, wherein the party controlling access to the platform sets the platform to an increased level of access to the functionality of the platform in response to the receipt of the indication of approval. For example, a platform that had previously been useful only for bench testing may have the level of access modified so as to be useful for animal studies. In addition, the party controlling access to the platform may set a customer charge (e.g., a certain amount of currency or value per level of access) according to the level of access of the platform, which charge may be assessed before, at the same time, or after the increased level of access is set. The customer charge may vary according to the level of access permitted, or may be a set amount for each increase in level of access.

Before returning to block 506, a determination may be made if the approval process is complete. For example, it may be determined at block 510 that the level of approval received was approval to market the medical device. Such approval would indicate that restricted use of the platform, as controlled by the party controlling access, is complete. In such a circumstance, the method 500 would continue to block 512, wherein the new sensor and/or control algorithm are marketed. Alternatively, the method would return to block 506.

As noted above, the method 500 may facilitate the standardization of testing required for eventual approval of the sensor and/or therapy management algorithm. The method 500 also may provide a more consistent development process, with a system having uniform quality. Further, the method 500 may permit the manufacturer to leverage the innovation of a large number of users of the above-described system for new sensors and/or therapy management algorithms to be used with the manufacturer's commercial equipment. In return, the method 500 may permit innovators to leverage the expertise of the manufacturer in the form of a stable, standardized system for sensor and/or algorithm development, lowering the level of knowledge required by the innovators of the structure and operation of the manufacturer's equipment, such as the pump and pump controller in the embodiments described above. Further, the systems and method 500 described above may permit the innovators to more easily move their innovations to market, in that use of the system provided by the manufacturer should permit the manufacturer to more easily integrate the innovations into their existing product line and manufacturing processes.

Figure 9:
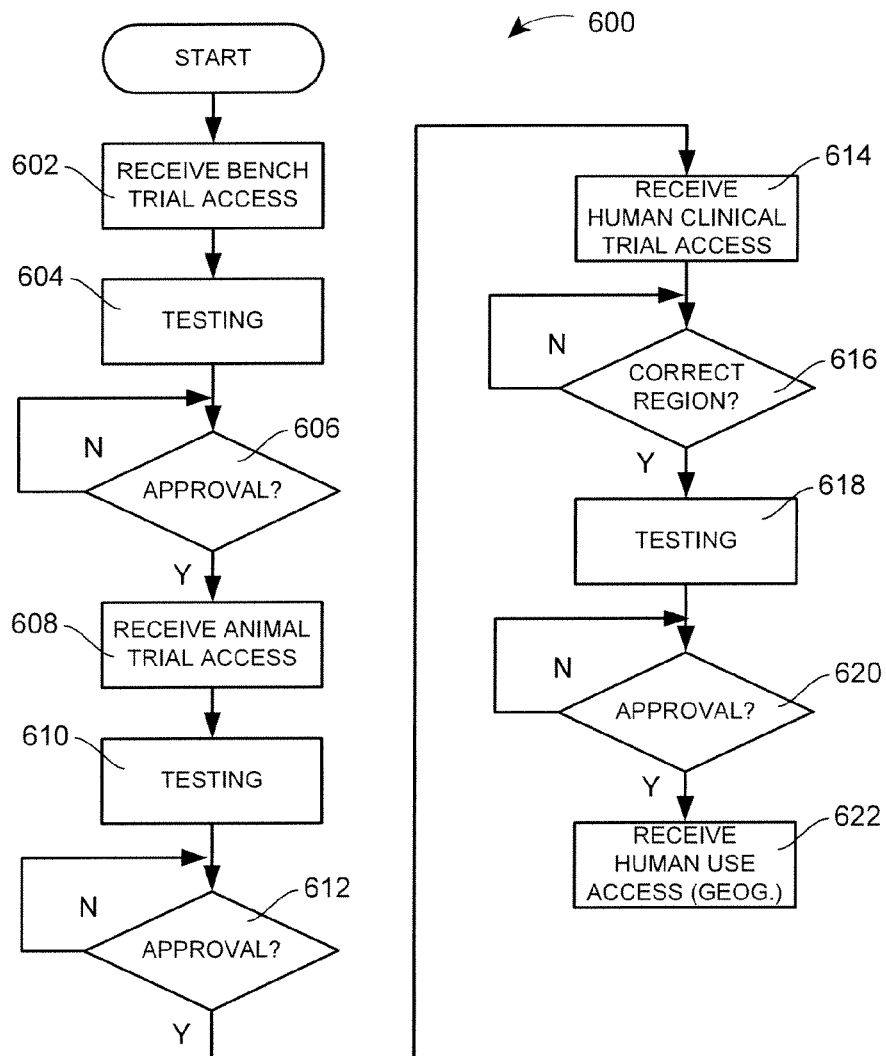
FIG. 9 is a flowchart of a operational process used by the systems according to the preceding embodiments.
Figure 10:
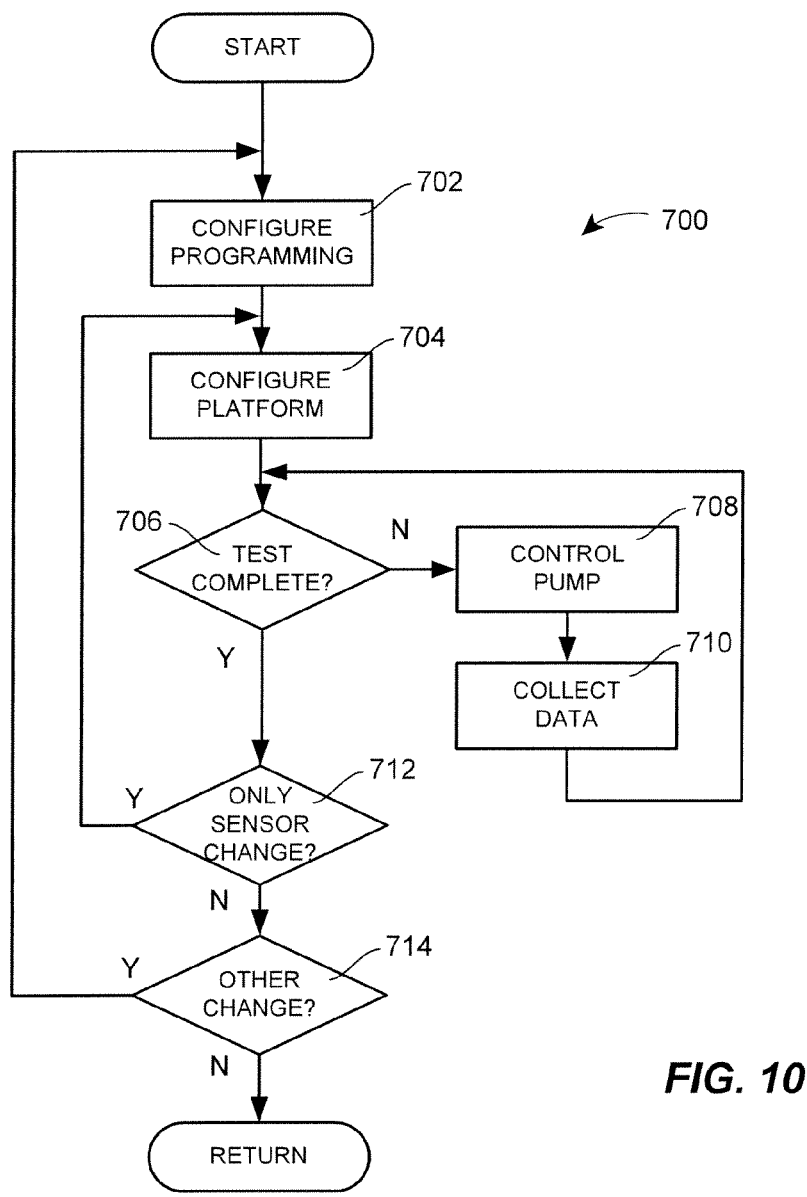
FIG. 10 is a flowchart of a testing sub-process used by the systems according to the preceding embodiments in carrying out the operational process of FIG. 9, for example.
Figure 11:
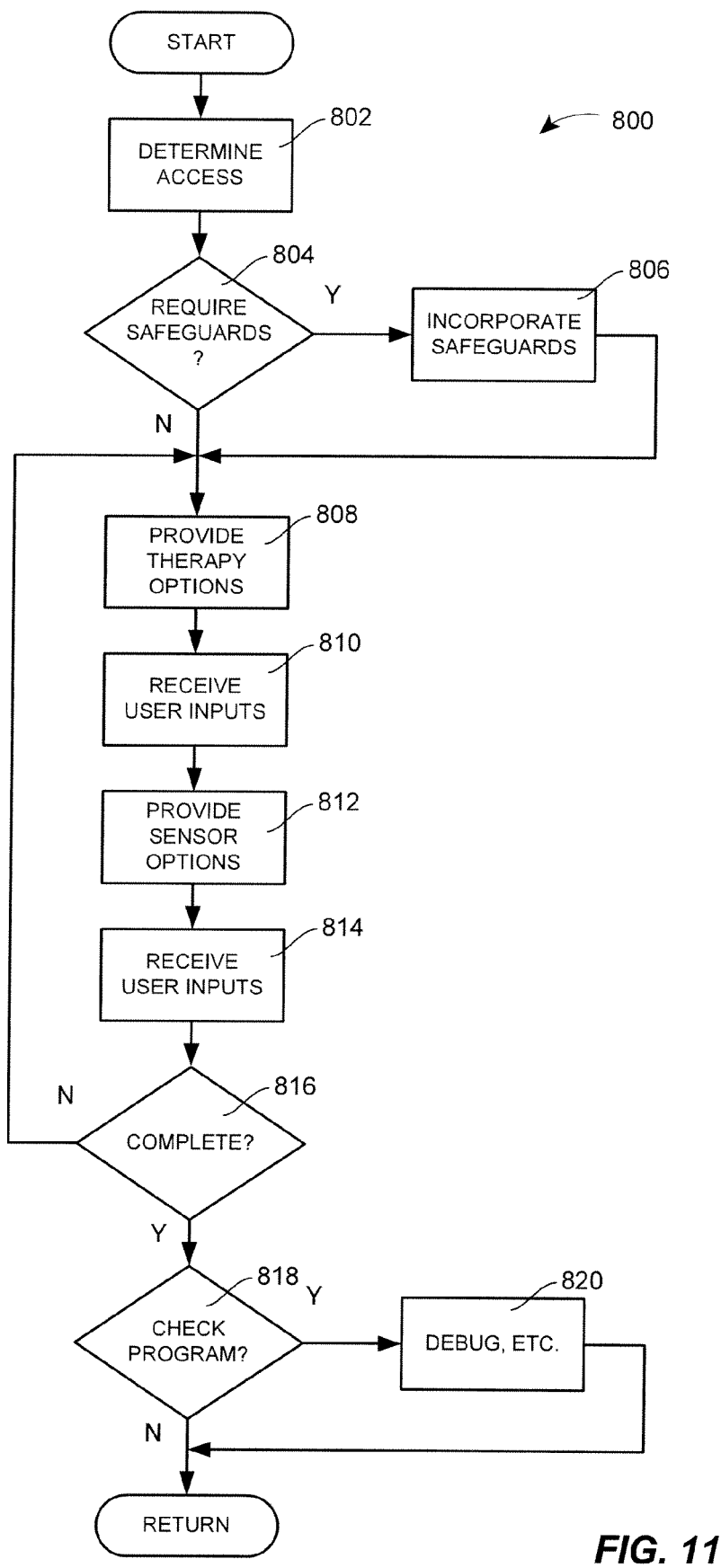
FIG. 11 is a flowchart of a programming configuration sub-process used by systems according to the preceding embodiment in carrying out the testing sub-process of FIG. 10, for example.

A further illustration of the operation (and hence the programming) of the therapy management development platform may be found in FIGS. 9-11. It will be appreciated, from the foregoing discussion as well as the disclosure relative to FIGS. 9-11, that the programming of the platform may involve the programming of a number of separate devices or processors (see the embodiments of FIGS. 1-6). Moreover, the programming may include software, and it may include firmware as well. Further, the programming may be in different programming languages, each in accordance with the device that will execute the programming or operate according to the programming. At a higher level, the programming may be procedural, object-oriented, event-driven, etc. However, it is possible (for example, in regard to the embodiment of FIG. 7) that the programming of the platform may involve the programming of a single device or processor using a single programming language.

Turning now to FIGS. 9-11 in detail, FIG. 9 provides a overview of the operation of, for example, the system 100 from initiation of development to use of the system 100, for example, in a healthcare setting with a patient. FIG. 10 illustrates the operation of the system 100 during the testing and development phase, wherein repeated iterations of testing and development may be performed using the system 100. FIG. 11 illustrates the operation of the system 100, and in particular the toolkit, to configure the control programming that will be executed during either the testing and development phase or the system 100 during normal commercial use.

Starting then with FIG. 9, a process of operation 600 (which, as mentioned above, may be reflected in the programming of the system 100) begins at block 602. At block 602, the system 100 receives a password, encryption key or the like that permits the system to provide a level of access to permit bench trials to occur. In certain instances, the system 100 may receive the password, encryption key or the like at the point of manufacture of the system 100. In other instances, the system 100 may receive the password, encryption key or the like after having been used in normal commercial use without the testing and development aspects of the system 100 having been used previously. In still other instances, the password, encryption key or the like may be used to change the level of access of a system 100 that had previously been used in a different level of access (e.g., animal trials).

In fact, it is important to note, as reflected in the discussion above, that the receipt by a particular system 100 (i.e., instance of the system 100) of a password or encryption key for animal trials, for example, does not require that the particular system to have first received a password or key corresponding to a level of access for bench trials. Similarly, a particular instance of the system 100 may receive a password permitting access to the functionality for human clinical trials or even human use (within a particular geographic location) without having received the passwords for bench or animal trials. Thus, it is not required that each instance of the system 100 necessarily be used for testing and development at each level of access, or that each instance be used for testing and development prior to human use.

Further, the process 600 illustrated in FIG. 9 is representative of the programming of an instance of a system 100 with the greatest degree of flexibility, permitting it to be used in all manner of trials and in normal commercial human use. However, it will be recognized that one or more of the blocks of the process 600 may be omitted in certain instances of the system 100, while that instance of the system 100 remains within the scope of this disclosure. For example, certain instances of the system 100 may include the functionality for bench and animal trials (but not human clinical trials or use), while other instances of the system 100 may be used for human trials (but not bench trials and animal trials). However, in each of these examples, the system 100 is still programmed to change between different levels of access to functionality based on the password, key, etc. received by the system 100.

Continuing on to block 604, the system 100 may now be used for bench testing. In regard to the aspects of testing and development represented by block 604 in process 600, reference is made to the process 700 of FIG. 10. Moreover, initial block 702 of the process 700 (programming configuration) is illustrated in greater detail in the process 800 of FIG. 11, which begins with the determination of the level of access at block 802. Consequently, the discussion continues with block 802 of the process 800.

As noted before, the level of access may be associated with certain lockouts. That is, the system 100 may include certain levels of functionality that may not be available during all phases of the development process. By administering the level of access (associated with the key or password), the manufacturer (or its development partner responsible for administration of the keys or passwords) can provide a system 100 with considerable functionality (in terms of programming and/or hardware) while preventing that functionality from being used where regulatory approval has not yet been obtained.

The precise operation of the system 100 at block 802 in determining the level of access will vary according to the nature of the key, password, etc. associated with the different levels of access. For example, the system 100 may have a series of passwords stored in an internal memory, one or more of the passwords associated with a particular level of access. The password received by the system 100 may then be compared with one of the internally stored passwords to determine whether or not access should be permitted, and if so, at what level. Alternatively, a public-private encryption key may be used to determine if access should be permitted, and if so, at what level.

Once this has been determined, the process 800 continues to block 804, where the system 100 determines if certain safeguards need to be implemented according to the level of access permitted. If safeguards need to be implemented at a particular level of access, then the process 800 continues to block 806. If not, then the process 800 continues to block 808.

As noted above, these safeguards may be in the form of lockouts relative to the functionality of the system 100 at lower levels of access. As an example of this type of safeguard, the system 100 may permit only virtual (physiological and sensor) data models to be used with the control programming during bench trials. As another limitation, the system 100 may only provide access to certain portions of the toolkit (e.g., certain libraries of functions, filters, etc.) according to the level of access permitted.

However, the safeguards may also come in the form of warnings or functional limitations that are implemented at higher levels of access, because human clinical trials or human use is involved. As an example of this type of safeguard, a warning message may be displayed prior to initiation of the pump, or certain ranges of pump operation, which were permitted during bench trials or animal trials, are prohibited by blocking control signals that exceed a predetermined operational range for the pump at that level of access.

Consequently, the safeguards may represent not only the prevention of certain actions or the limitation of certain functionality, but the requirement that certain actions be taken. Further, the safeguards may not only limit functionality at the lower levels of access, with greater freedoms at the higher levels of access, but the system 100 may instead impose greater limitations on functionality on the higher levels of access as well.

It will be recognized that the determination if safeguards are required and the incorporation of the safeguards at blocks 804, 806 is not limited to the particular position within the process 800 illustrated in FIG. 11. For example, the safeguards may be incorporated at a later stage in the process 800, as a check against the programming prepared in response to user selections (see blocks 808-814). Alternatively, the determination whether safeguards are to be incorporated and/or their incorporation into the programming may operate in parallel as a process in the background while the actions of blocks 808-814 operate in the foreground, rather than in series with the actions of blocks 808-814. As a further alternative, the actions of blocks 804, 806 may occur as each user selection is received by the system 100 at blocks 810, 814.

Once the safeguards, if any, have been incorporated at block 806, the process 800 continues to blocks 808-814. While a particular arrangement of the blocks 808-814 has been selected for illustration and discussion, it will be recognized that the sequential order of actions represented by blocks 808-814 is merely for ease of exposition, not by way of limitation on the disclosure herein, as was the case with the determination and incorporation of safeguards as blocks 804, 806. The blocks 812, 814 may precede blocks 808, 810 in all instances, or blocks 808, 812 may occur in parallel (see, e.g., FIG. 4), with order of the blocks 810, 814 occurring in accordance with the receipt by the system 100 of inputs from the user.

At block 808, the system 100 provides the user with one or more (typically a plurality) of therapy options. As discussed above, with reference to FIG. 4, the options may include a plurality of potential therapy control algorithms, and may be displayed graphically to the user on an output device. The user may express his or her selection of particular items from the therapy options by toggling a check box or other input representation using an input device (e.g., a mouse, stylus and pad, etc.). The system 100 will receive the user input at block 810, and the process 800 proceeds to block 812.

Similar to blocks 808, 810, the actions of blocks 812, 814 involve providing one of more (again, typically a plurality) of sensor options and receiving a user input relative to the desired options to be incorporated into the programming of the system 100. With reference to FIG. 4, the options may include a plurality of sensor parameter options as well as a plurality of sensor data filtering options. The user may again express his or her selection of particular items from the therapy options by toggling a check box or other input representation using an input device (e.g., a mouse, stylus and pad, etc.). The system 100 will receive the user input at block 814, and the process 800 proceeds to block 816.

At block 816, the system 100 determines if the user has completed his or her selection of the control and sensor options (or additional options, such as display options, if provided). The system 100 may determine if the selection process is complete by determining if a particular input has been received from the user via an input device. For example, the system 100 may display a button within a graphical user interface on an associated output device (e.g. monitor), which the user may manipulate via an input device (e.g., mouse) so as to send an input to the system 100 that the user has completed his or her selections. Alternatively, the button may be in the form of a physical input (e.g., push button) that is connected to the system 100, and which is used to provide an input to the system 100 that the user has completed the process. As a still further alternative, the system 100 may determine that the user has completed the process when the system 100 has received the user's input representative of the selection of the therapy and/or sensor options.

If the system 100 determines that the user has not completed the selection process at block 816, the process 800 returns to block 808. Alternatively, if the system 100 determines that the user has completed his or her selections, the process 800 proceeds to block 818.

At block 818, the system 100 reviews the programming assembled according to the user inputs received at blocks 812, 814 to determine if the programming is to be checked prior to returning to the process 700. If the program is to be checked, then the process proceeds to block 820. On the other hand, if the program does not need to be check, the process returns to the process 700. For example, where the changes represent scaling a particular output display, the program may not need to be checked prior to returning to the process 700; alternatively, if a completely different control algorithm has been selected, checking may be required.

At block 820, the system 100 may check the programming assembled, for example, for any errors that will prevent a processor from operating according to or executing the programming during testing. As with the safeguards discussed above, the position of the determination as to whether the program is relatively error-free (or error-prone) does not necessary have to occur in the exact place in which it is located in the flowchart of FIG. 11. As will be recognized, the action of checking the program, for errors for example, may occur in parallel with the actions of blocks 808-814. However, for ease of explanation, blocks 818, 820 have been placed at the end of the flowchart of FIG. 11.

Returning now to FIG. 10, the process 700 may proceed to block 704, wherein the system 100 may configure the remainder of the system 100 after the completion of the programming configuration that occurred at block 702. For example, the system 100 may upload the programming prepared at block 702 to the memory of the processor as part of the configuration of the system 100. In addition, the system 100 may activate certain sensor inputs according to the programming uploaded to the controller, or may search the sensor inputs to determine if the sensor, etc. is present. The system 100 may also determine whether or not it is necessary to provide power to the sensor from the power supply associated with the system 100. Other actions may be taken by the system 100 at this point to prepare for communication between the elements of the system 100 according to certain proprietary or standardized protocols.

Once the system 100 has been configured at block 704, the testing may begin at block 706. If the system 100 determines at block 706 that the testing is on-going, then the process 700 continues to blocks 708, 710 where the system controls the pump associated therewith according to the control options selected and collects data from the sensor according to the sensor options selected. If the system 100 determines that the testing is completed, then the system 100 proceeds to block 712.

At block 712, the system 100 determines if the user only wishes to make a change or has only made a change to the sensor. For example, the system 100 may determine if only a sensor change has been made, if no new program has been uploaded to the controller, by detecting that the sensor has been decoupled and recoupled to the system 100. Alternatively, the user may manipulate an input device that provides an input indicative of the user's decision to alter only the sensor, and the system 100 may determine that only the sensor is to be changed upon receipt of that input. If only a sensor change has been made, then the process 700 may return to the configuration block 704, and a new cycle of testing may occur at blocks 706, 708, 710.

Similarly, at block 714, the system 100 may determine if the user desires to make changes or has made changes to the sensor and the programming of the system 100, or just the programming. As was the case at block 712, the system 100 may monitor the programming of the controller and the connection of the system 100 to the sensor to determine if the programming or if both the programming and the sensor have been changed. Alternatively, the user may manipulate an input device and the system 100 may determine, according to the receipt of an input from the input device, that the user has modified the programming or the programming and the sensor. If so, the process 700 may return to block 702; if not, the process 700 may return to the process 600.

Returning then to the process 600, and in particular the block 606, the system 100 may determine if further regulatory approval has been received. The system 100 may determine that regulatory approval has not been received if no new access has been received. Alternatively, the system 100 may determine that approval has been received if a new key or password associated with a new level of access associated with further regulatory approval has been received. The system 100 may receive the key or password associated with animal trial access at block 608.

The process 600 continues to further testing at block 610, with the process of the testing at block 610 again being reflected in the process 700 (and, potentially, the process 800). Where the system 100 was used previously for the development of the control programming and sensor for bench trials (as it was according to this embodiment, at blocks 602, 604), the system 100 may pass quickly through certain actions included within the process 700. For example, based on the results of the bench testing, the user may not wish to reconfigure the control programming or the sensor configuration. As such, the system 100 may perform the actions of blocks 702, 704 of the process 700 relatively quickly, and the process may proceed almost directly to block 706.

However, as mentioned above, different safeguards may be included as different levels of access are achieved. In such a case, even though the user may not have any desired changes required to the programming, the system 100 may be required to execute parts of process 800 so as to incorporate these safeguards into the programming. As a result, this may lead the system 100 to carry out the actions of blocks 808-814 because new options may be included or imposed because of the safeguards incorporated by the system at block 806, further requiring the system to carry out the actions of blocks 816-820 as well.

Once the testing has been completed at block 610, the system 100 again awaits approval at block 612. Upon receipt of the human clinical trial access (at block 614), the system 100 may determine that the process 600 may proceed to block 616.

At block 616, the system 100 may determine if the access received at block 614 is appropriate for the geographic location where the system 100 is located. That is, certain types of regulatory approval, in particular that involving human clinical trials or human use, are usually granted for a limited geographic region (which may or may not correspond to the geographic region associated with a single national authority). As such, an instance of a system 100 operating with a particular control programming and sensor in, for example, the United States may not be approved for human clinical trials even though a system 100 with similar programming and sensor is approved for use in Europe. Consequently, it may be necessary for certain types of access to be associated with correct geographic placement of the system 100 before the system 100 will permit the functionality with a particular level of access.

The determination as to whether the system 100 is disposed in the proper geographic location may be performed in a number of different ways. For example, the system 100 may simply require receipt of an input from the user in response to a prompt for information regarding the geographic location where the testing is to occur (and hence where the system 100 will be located). The system 100 may then check the input with information regarding the permitted geographic location associated with the key or password corresponding to the approval obtained.

Such a determination obviously operates on an "honor" system, which may be insufficient for certain regulatory authorities. Consequently, the system 100 may include or may be equipped with a global positioning system (GPS) receiver, which may utilize a satellite-based navigation system to provide the positioning information regarding the associated system 100 with sufficient accuracy so as to permit the system 100 to determine the geographic location of the system 100. The system 100 may then check the information obtained from the GPS receiver against the permitted geographic location associated with the key or password corresponding to the approval obtained. It will be recognized that the use of a GPS receiver is simply one of a number of options that may be used to determine the location of the system 100 without involving (or relying on) the user input.

It will also be recognized that, as explained above, the system 100 may include one or more elements that are not located physically in the same geographic location. To this end, the geographic location of certain elements of the system 100 may be more important to the determination of block 616 than others. For example, the tool kit which is part of the system 100 and may be used in carrying out the process 800 may be located on a computer 140 that is physically remote relative to the pump 114, pump controller 110, sensor 106 and interface 104. Further, the location of the pump 114, pump controller 110, sensor 106 and interface 104 may be of greater (or exclusive) relevance to the approval granted than the position of the computer 140 operating according to the tool kit of the present disclosure. Consequently, the system 100 may be programmed to determine the geographic location of parts or elements of the system 100 relative to the approval granted, rather than determining the geographic location of the entire system 100. To this end, in the embodiment where a GPS receiver is associated with the system 100 to permit the system 100 to determine the geographic location of the system 100, the GPS receiver may be associated (by attachment or disposal in a common housing) with those elements of the system 100 that are relevant to the determination as to whether the system 100 is located in a proper geographic location.

Once the system 100 has completed the inquiry of block 616, the process may proceed to block 618, which is similar to blocks 604, 610. After the testing is completed, the process 600 continues to block 620, where the system 100 determines if approval has been obtained for human use outside of the clinical study setting. If such approval is obtained, the process 600 proceeds to block 622, where the system 100 receives the human use access.

As noted above, the human use access received by the system 100 at block 622 will likely be restricted according to a particular geographic location. Consequently, the system 100 may carry out a determination, similar to that of block 616, as to whether the system 100 (or the relevant portion of the system 100) is located in the proper geographic location relative to the approval obtained and the access granted. To this end, the same types of actions described above relative to block 616 may also occur at block 622.

As noted above, while the therapy management development platform has been discussed relative to infusion therapy management, other forms of therapy management development may be facilitated through the use of a similar platform. For example, inhalation therapy management and renal therapy management development may benefit through the use of a similar therapy management development platform as explained in greater detail below.

In regard to inhalation therapy management, a system for inhalation therapy management may include a vaporizer that is connected to a source of an anesthetic agent. The vaporizer vaporizes the anesthetic agent, mixing it with a carrier gas, to create a gas which will be inhaled by a patient as part of an inhalation therapy, such as may be administered to the patient in an intensive care unit, for example. In particular, the gas may pass through an endotracheal tube disposed through the patient's mouth; alternatively, the gas may pass through a mask disposed over the patient's mouth and nose. The tube or mask may be associated with a sensor, and may also be associated with an adsorbent media. The sensor is coupled to a vaporizer controller that may vary the amount of gas administered to the patient via the tube or mask by the vaporizer in accordance with the signal received from the sensor.

In operation, the patient would inhale gas provided by the vaporizer through the tube or mask. Upon exhale, perhaps 70 to 80 percent of the inhaled gas is expelled by the patient. The adsorbent media associated with the tube or mask may capture a certain fraction of the anesthetic exhaled. The next time the patient inhales, the anesthetic captured by the media is inhaled by the patient. The inhalation therapy management system may determine the amount of anesthetic contained in each exhale or inhale through the use of the sensor associated with the tube or mask. Based on this determination, the vaporizer controller may add further gas from the vaporizer.

Such an inhalation therapy management system has certain similarities with the infusion therapy management systems described above. In particular, the inhalation therapy management system relies on one or more sensors that determine a characteristic of the therapy or the patient. For example, the system described above includes a sensor to determine anesthetic content/concentration in the inhale or the exhale. Potentially, other sensors may be used as well, for example blood oxygen sensors, blood pressure sensors, etc. Furthermore, the vaporizer controller uses a control algorithm to vary the gas provided to the patient from the vaporizer in response to the signals received from these sensors.

As a consequence, the use of a therapy management development system according to any of the embodiments of FIGS. 1-7 may be useful in developing an inhalation therapy management system as well. Rather than interacting with the pump controller, the therapy management development module would interface with the vaporizer controller. While the specifics of the sensors and control algorithms used may vary, the general framework and method of use of such an inhalation therapy management development system and method would operate along lines similar to those described above relative to the infusion therapy management development system. Consequently, the different embodiments and variations to those embodiments discussed above would apply with equal force to the design and use of a development system for inhalation therapy management.

As for renal therapy and renal therapy management, similar comments could be made regarding the operation of the renal therapy management system relative to the infusion therapy management system described above, as well as usefulness of the therapy management development system for use with such renal therapy management systems.

For example, one conventional renal therapy is hemodialysis. In hemodialysis, a blood pump is used to draw blood from the patient, pass the blood through a dialyzer, and then return the blood to the patient along a first circuit. In a second, separate circuit, a separate pump is used to circulate dialysate through the dialyzer. In the dialyzer, waste products pass through a membrane/filter from the blood into the dialysate. A controller may be coupled to both pumps and to sensors disposed in both circuits. The sensors may monitor flow rates, and the conductivity, temperature and pH of the dialysate. The controller may vary the operation of one or both of the pumps in accordance with signals received from the sensors.

As was the case with inhalation therapy, the inclusion of a controller that varies operation of a component (in the case of hemodialysis, the blood pump and the dialysate pump) in accordance with sensor data is believed to make the above-mentioned development systems and tools described in the context of infusion therapy useful with renal therapies as well. Moreover, given the similarities between hemodialysis and aphaeresis, it is also believed that the therapy management development systems and methods described above may be useful relating to aphaeresis therapy management as well.

What is claimed is:

1. A method of providing therapy management development, the method comprising:
   providing a computerized therapy management development platform including at least (i) a pump controller including a first processor, and (ii) an interface module including (a) a second processor, (b) a pump controller module input/output interface, and (c) a module-sensor input/output interface, the interface module coupled to the pump controller via the pump controller module input/output interface;
   performing one or both of:
   (a) coupling a sensor-under-test to the module-sensor input/output interface, the sensor-under-test unapproved for therapeutic use; and
   (b) programming the pump controller with an algorithm-under-test, the algorithm-under-test unapproved for therapeutic use;
   setting the computerized therapy management development platform to a first level of access to facilitate a first stage of testing of the sensor-under-test and/or the algorithm-under-test, the first level of access providing first functionality;
   testing one or more aspects of the sensor-under-test and/or the algorithm-under-test and receiving testing results; and
   setting the computerized therapy management development platform to a second level of access, in response to an indication of approval to perform a second stage of testing, to facilitate the second stage of testing of the sensor-under-test and/or the algorithm-under-test, the second level of access providing second functionality different from, but possibly inclusive of, the first functionality.

2. The method according to claim 1, wherein performing one or both of (a) and (b) comprises performing (a).

3. The method according to claim 2, further comprising changing the operation of a control algorithm.

4. The method according to claim 1, wherein performing one or both of (a) and (b) comprises performing (b).

5. The method according to claim 4, wherein programming the pump controller with the algorithm-under-test comprises programming the controller using a development toolkit configured to permit a program to be written by a user through the manipulation of a GUI in combination with a library of standardized input commands, output commands, and procedure commands.

6. The method according to claim 1, wherein the sensor-under-test and/or the algorithm-under-test are being tested for integration with a commercial product already existing at the time that the testing occurs.

7. The method according to claim 1, wherein performing one or both of (a) and (b) comprises performing (a) and (b).

8. The method according to claim 1, further comprising setting the computerized therapy management development platform to a third level of access, in response to a second indication of approval, to facilitate a third stage of testing of the sensor-under-test and/or the algorithm-under-test, the third level of access providing third functionality different from, but possibly inclusive of, the second functionality.

9. The method according to claim 8, wherein the second indication of approval indicates regulatory approval and wherein the third functionality facilitates use of the sensor-under-test and/or the algorithm-under-test in a commercial product.

10. The method according to claim 1, wherein the interface module may be customizably programmed to receive different data from the sensor-under-test, to provide different instructions to the pump controller to vary the operation of the pump, or both.

11. The method according to claim 1, wherein the indication of approval is an encryption key, the interface module programmed to change the level of access in response to receipt of the encryption key from a remote computer.

12. The method according to claim 1, wherein:
   receiving the indication of approval comprises receiving an indication of approval associated with a geographic location for the pump controller and interface module; and
   setting the computerized therapy management development platform to the second level of access comprises determining if the pump controller and the interface module are disposed in the geographic location, and setting the computerized therapy management development platform to the second level of access only if it is determined that the pump controller and interface module are disposed in the geographic location.

13. The method according to claim 1, wherein:
   setting the computerized therapy management development platform to the first level of access comprises setting the computerized therapy management development platform to the first level of access according to a determination made by a first party, separate from a second party that modifies the operation of a medical device, that the second party has received approval from a governmental or commercial organization that oversees testing of medical devices prior to marketing to have access to the first level; and
   setting the computerized therapy management development platform to the second level of access in response to receipt of the indication of approval comprises setting the computerized therapy management development platform to the second level according to a determination made by the first party that the second party has received approval from the governmental or commercial organization to proceed to the second level of access.

* * * * *

UNITED STATES PATENT AND TRADEMARK OFFICE
CERTIFICATE OF CORRECTION

PATENT NO. : 10,546,101 B2
APPLICATION NO. : 14/808206
DATED : January 28, 2020
INVENTOR(S) : Ross G. Krogh et al.

Page 1 of 1

It is certified that error appears in the above-identified patent and that said Letters Patent is hereby corrected as shown below:

On the Title Page

Column 1, Item (60), "(60)" should be -- (63) --.

Signed and Sealed this
Thirtieth Day of June, 2020

Andrei Iancu
*Director of the United States Patent and Trademark Office*